United States Patent [19]

Borodulin et al.

[11] Patent Number: 4,942,869
[45] Date of Patent: Jul. 24, 1990

[54] EXPANDABLE URETHRAL BOUGIE

[75] Inventors: German Borodulin, San Francisco; Alexander Shkornik, San Mateo; Maxim D. Persidsky, San Francisco; Perinchery Narayan, San Rafael, all of Calif.

[73] Assignee: Urological Instruments Research, Inc., San Francisco, Calif.

[21] Appl. No.: 278,826

[22] Filed: Dec. 2, 1988

[51] Int. Cl.$^5$ .............................................. A61H 1/00
[52] U.S. Cl. .................................................... 128/43
[58] Field of Search ...................................... 128/43–44, 128/341, 345, 343, 303.11, 32; 604/104–109, 116, 117, 93

[56] References Cited

U.S. PATENT DOCUMENTS

| 1,191,683 | 7/1916 | Finley . |
| 1,716,143 | 6/1929 | Marosy . |
| 1,758,082 | 5/1930 | McGowen . |
| 1,972,391 | 9/1934 | Morse . |
| 3,495,586 | 2/1970 | Regenbogen . |
| 4,043,338 | 8/1977 | Homni et al. . |
| 4,154,242 | 5/1979 | Termanini . |
| 4,224,931 | 9/1980 | Nelkin . |
| 4,432,758 | 2/1984 | Finegold . |
| 4,607,626 | 8/1986 | Borodulin et al. .............. 128/43 |
| 4,705,029 | 11/1987 | Borodulin et al. .............. 128/43 |

FOREIGN PATENT DOCUMENTS

| 73751 | 9/1917 | Austria . |
| 458663 | 4/1928 | Fed. Rep. of Germany . |
| 640126 | 12/1936 | Fed. Rep. of Germany . |
| 520263 | 6/1921 | France . |
| 265400 | 11/1929 | Italy . |

Primary Examiner—E. H. Eickholt
Attorney, Agent, or Firm—Townsend & Townsend

[57] ABSTRACT

A mechanically-expandable urethral bougie (10) especially useful for dilation of urethral strictures comprises a probe formed from two elongated rods (12, 14) connected at their one end, the rods having a semicircular cross-section and grooves at the mating surfaces. These grooves form a guide slot 26 for a core element (28) which has wedging elements (34, 36) engageable with camming surface of the rods. The end of the probe opposite to the connected ends of the rods is provided with a drive mechanism for axial movement of core element (28). When the core elements move in the axial direction, engagement of its wedging elements (34, 36) with camming surfaces of the rods causes expansion or dilation of the probe, depending on the direction of movement. At its front end, the bougie is provided with a leader (52) of a smaller diameter and higher flexibility than the rest of the probe. The leader facilitates the insertion of the bougie into the patient's urethra. Another feature of the invention is a provision of a longitudinal channel which is formed either in one of the probes or in the core element. When the probe penetrates into the bladder, dripping of urine through this channel indicates to the urologist the fact of penetration of the probe into the bladder. Another feature of the probe is the provision of means for positively locking the rods and core in an assembled state.

38 Claims, 2 Drawing Sheets

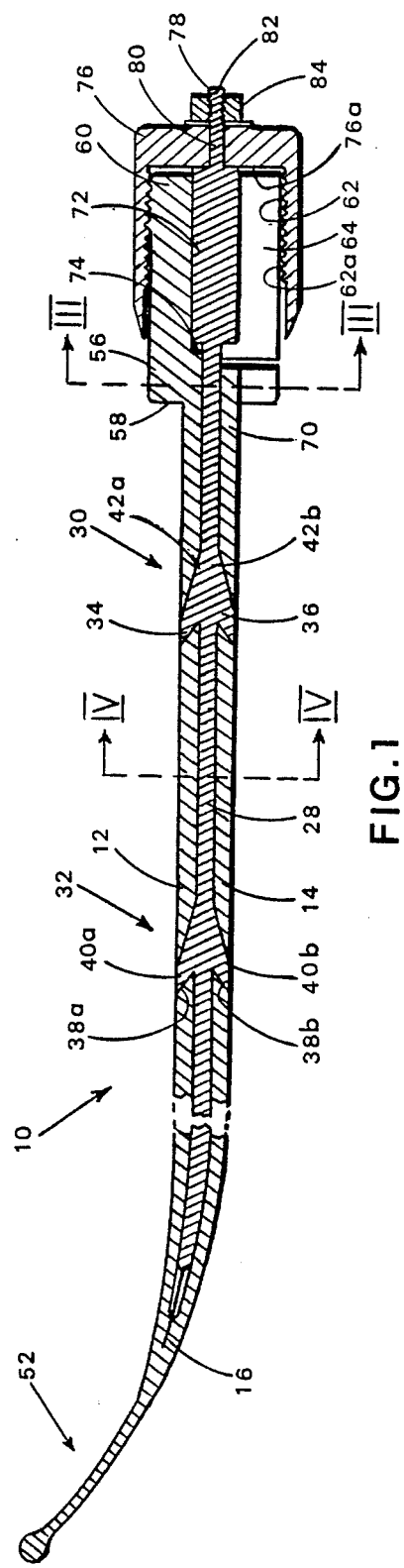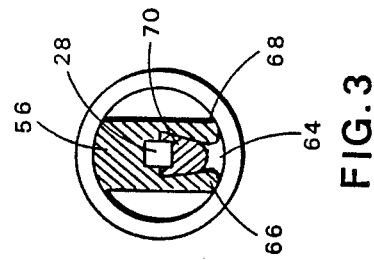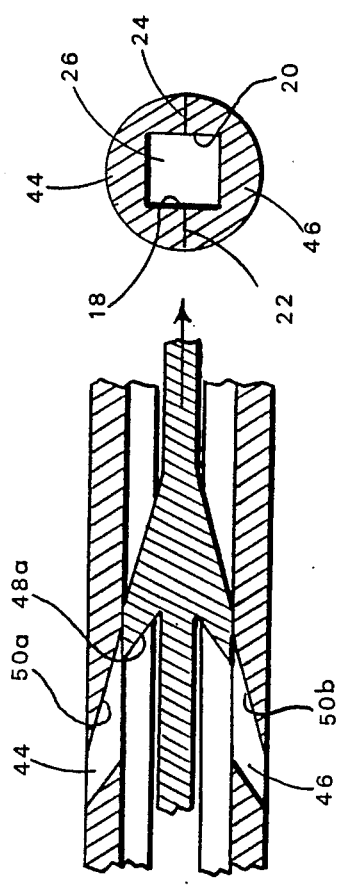
FIG. 1
FIG. 2
FIG. 3
FIG. 4

EXPANDABLE URETHRAL BOUGIE

CROSS-REFERENCES TO RELATED APPLICATIONS

This fifth application relates to the improvement of an expandable urethral bougie disclosed in fourth application Ser. No. 896,810 filed Aug. 15, 1986, now U.S. Pat. No. 4,705,029, granted on Nov. 10, 1987, which, in turn, is a continuation-in-part of third application Ser. No. 861,871 filed on May 12, 1986, now abandoned. Said third application is a division of a second application Ser. No. 778,760 filed on Sept. 23, 1985, now U.S. Pat. No. 4,607,626, granted on Aug. 26, 1986. Said second application is a U.S. continuation-in-part of a first application, Ser. No. 621,842, filed on June 18, 1984, now abandoned.

BACKGROUND

1. Field of the Invention

This invention relates to medical instruments, particularly to urological probes (bougies) for dilation of the urethra.

2. Description of Prior Art

Urethral strictures, especially postraumatic ones, are very dense, rigid, and resistant to stretching. They are localized mostly in the membranous or bulbous parts of the urethra.

A non-surgical method for treating urethral strictures, known as bougienage, involves probing such strictures with elongated members or probes to enlarge them.

Such probes are known as bougies and prior-art, conventional bougies, are shown, e.g., in the textbook "Urology", 3rd ed, v.1. p. 242, M. F. Campbell and J. H. Harrison, etc. (Saunders, 1970). They comprise solid metal (or plastic) rods which are shaped to accommodate the physiological curvature of the urethra. Since in males the urethra's outer part is within the pendulus of the penis, which is highly flexible, this outer part can be bent or straightened, as necessary. The urethra's inner part extends around (behind) the pubic articulation and thus is curved. In other words, conventional bougies generally comprise a straight portion extending from the handle, followed by a curved portion adjacent to the tip. This shape corresponds to the urethra when the penis is straightened, i.e., starting at its penile outlet, the urethra is straight and then curved (roughly C-shaped).

Despite the correspondence in shapes, the insertion of a conventional bougie in males is a very complicated and painful operation, requiring high skill and concentration. Usually, the urologist will employ a set of bougies of gradually increasing diameters. The results of treatment with such instruments are not always positive, complications such as bleeding, injuries, urinary fever, prostatitis, epididymitis, etc., may occur. Even in females, whose urethras are shorter and straighter, many of these difficulties are encountered.

To obviate these disadvantages, the authors of the present invention have developed a series of new expandable urethral bougies described in the above-mentioned U.S. Pat. No. 4,705,029. These bougies comprise a probe composed of two rods pivotally connected together at one end and having a core element between the rods with wedging elements. The core element is connected to a mechanism which moves it in the axial direction so that the rods are expanded by the above-mentioned wedges, and thus expand the urethra into which the bougie has been inserted. The expandable bougie is made from a plastic material and can be supplied to urologists in a sterilized and disposable form.

Although the plastic, disposable mechanically expandable bougies are universal, convenient to use, and what is most important, can substitute a whole set of conventional bougies, they still have some disadvantages. For example, the urologist does not know whether or not the distal end of the bougie has penetrated into the bladder. Insertion of the probe into the urethra presents some problems, and in order to facilitate this procedure, it is desirable to provide the bougie with a pilot portion or leader used for guiding the bougie during its insertion into the urethra. As the probe consists of three separate longitudinal elements, i.e., two rods and a core element, these elements, especially when they are made from plastic, are extremely flexible. When the bougie is within the urethra, it is compressed or squeezed by the urethral walls. Nevertheless, the above-mentioned three elements are not locked positively, and it is possible under certain circumstances that during withdrawal of the bougie from the urethra, the core element may come out from the guide groove and traumatize the urethra.

OBJECTS AND ADVANTAGES OF THE INVENTION

Accordingly, one main object of the invention is to provide an improved expandable urethral bougie for treating urethral strictures and for general expansion of the urethra prior to transurethral operations. Further objects are to provide bogies which have means indicating that the distal end of the bougie has penetrated into the bladder, and which have a mechanism for positive locking of rods and the core element together within the urethra after completion of the dilation and prior to withdrawal of the bougie from the urethra. Still a further object of the invention is to provide bougies which have a pilot element or leader serving to guide the distal end of the bougie during its insertion into the urethra. Another object of the invention is to provide bougies in which the leader at the same time serves as an indicator of penetration of the bougie into the bladder. Yet another object is to provide bougies which are made from plastic and can be supplied in a sterilized and disposable form. Other objects and advantages of the invention will become apparent from a consideration of the ensuing description and drawings.

BRIEF DESCRIPTION OF DRAWINGS

FIG. 1 is a general longitudinal sectional view of a flexible plastic bougie according to the first embodiment of the invention.

FIG. 2 is a fragmentary view of a bougie of FIG. 1 with positions of cams of the rods and wedges of the core element during expansion of the probe.

FIG. 3 is a cross-sectional view taken along line III—III of FIG. 1.

FIG. 4 is a cross-sectional view taken along line IV—IV of FIG. 1.

DESCRIPTION OF THE URETHRAL EXPANDABLE BOUGIE OF FIGS. 1 TO 4

Figure 5:
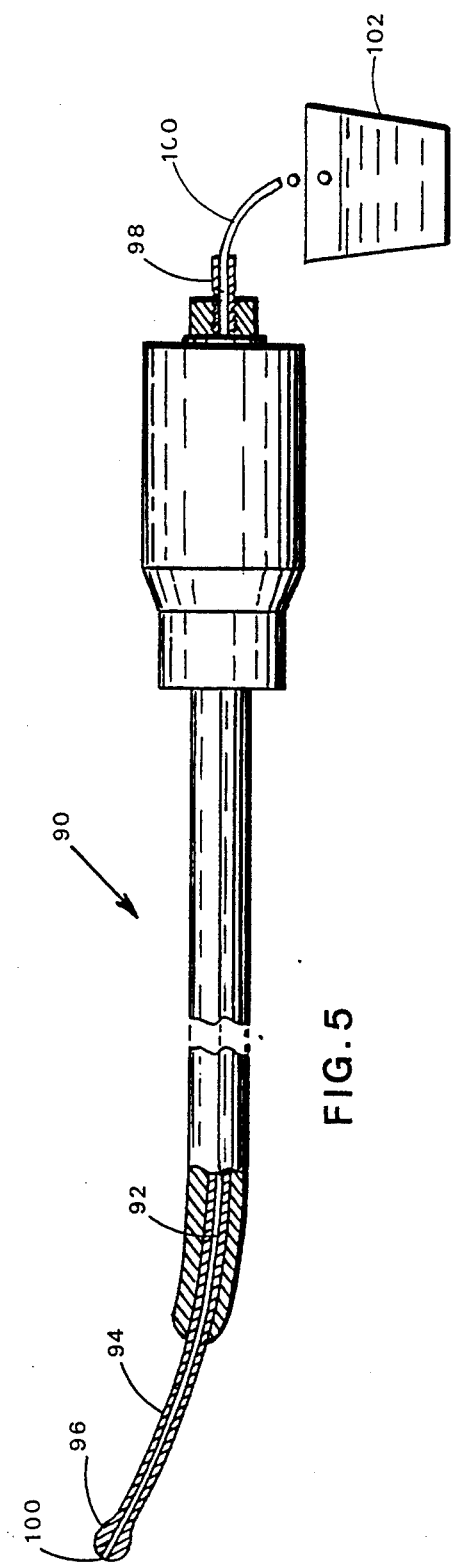
FIG. 5 is a side view of a bougie in accordance with the second embodiment of the invention.

FIG. 1 is a longitudinal sectional view of a urethral expandable bougie 10 made in accordance with the first embodiment of the invention. The bougie is formed of two rods, i.e., an upper rod 12 and a lower rod 14.

As shown in FIG. 4, each rod has a semicircular cross-section. When rods 12 and 14 are placed adjacent to one another flat sides facing, they form a complete circle. In their longitudinal view the rods in assembled state correspond to the shape of a conventional urological bougie, i.e., to the shape of the urethra. At their front ends, i.e., the left end in FIG. 1, the rods are interconnected. Such interconnection can be formed by a permanent or disconnectable pivot (in case of metal), or by thermal fusion or an adhesive substance 16 (FIG. 1) acceptable for medical applications (in case of plastic).

The rods have guide grooves 18 and 20 (FIG. 4) on their mating flat surfaces 22 and 24. When the rods are assembled face-to-face, these grooves form a closed rectangular guide slot 26. Slot 26 runs for about 9/10 the length of the rods, i.e., to the point of their interconnection at 16. In one embodiment the rods were 33.6 cm long (horizontal length) and slot 26 was 29.9 cm long. The grooves are shallower in the first third part, i.e., the straight portion of the bougie. Specifically, they are about 1.5 mm deep in the first third of the bougie and about 2.0 mm deep for the rest of the bougie.

A central rod or core element 28 is inserted into slot 26. Core element has several camming or wedging elements. For simplicity of the drawing, only two such wedging elements 30 and 32 are shown. It is understood that normally four or five wedging elements are used to provide uniform expansion and, as will be explained later, locking of the bougie elements. As both wedging and camming elements 30 and 32 are identical, only one of them, i.e., element 30, will now be described.

Wedging element 30 has two camming lobes 34 and 36, which project in opposite directions radially and symmetrically with respect to each other. Each lobe is shaped as a saw tooth inclined toward the front end of the the bougie. More specifically, lobes 34 and 36 have respective rearwardly inclined front surfaces 38a and 38b, flat peripheral surfaces 40a and 40b, and rear camming surfaces 42a and 42b. In one embodiment, front surfaces were inclined at an angle of 30° to the longitudinal axis of the bougie, flat surfaces had an axial length of 4 mm, and rear camming surfaces 42a and 42b were inclined at an angle of about 25° C. to the longitudinal axis of the bougie. It is understood, that these dimensions are given only as examples, and do not limit the scope of the invention.

Rods 12 and 14 have respective side through holes only two of which, i.e., holes 44 and 46 are shown in FIG. 2. It is understood that the number of such holes corresponds to the number of the camming lobes on core rod 28. Each hole 44 and 46 exactly corresponds in its shape and inclination to corresponding camming lobes. For example, hole 44, which corresponds to camming lobe 34, has a first surface 48a inclined in the same direction and at the same angle as surface 38a of the camming lobe 34, and a second or camming surface 50a which is inclined at the same angle and in the same direction as surface 42a of the lobe. Longitudinal length of each hole over the periphery of each rod is equal to the length of flat portions 40a and 40b of the corresponding lobes. It is understood that in a plan view each hole has a rectangular shape with the length of the rectangular opening equal to the length of flat portions 40a and 40b and the width of the rectangular opening equal to the width of core rod 28. Positions of openings 44 and 46 are shown in FIG. FIG. 4 by broken lines.

At the front or interconnected end, the probe formed by two rods 12 and 14 has a guiding element or leader 52. Leader 52 is more flexible and thinner than the remaining part of the bougie and may have a rounded spherical head 54 at tip. The leader serves to facilitate insertion of the bougie into the urethra.

At its rear end, the right end in FIG. 1, upper rod 12 has a portion 56 of an increased diameter. As shown in FIG. 3, which is a cross-sectional view along line III—III of FIG. 1, portion 56 is reduced to a U-shaped configuration at the front part 58 and has the shape of a complete cylinder at the rear part 60. Rear part 60 has an external thread 62 and a radial slot 64 (FIG. 1 and FIG. 3). At front part 58, side elements 66 and 68 slightly converge toward each other, so that the portion of slot 64 in this part has a triangular configuration with the base of the triangle at the bottom of the slot.

Lower rod 14 is shorter than upper rod 12 and is cut at the end of above-mentioned front part 58 of the increased-diameter portion 56 of the upper rod. As shown in FIG. 3, a rear end 70 of lower rod 14 is inserted into slot 64 of the upper rod. Rear end 70 also has an essentially triangular configuration which conforms the triangular shape of slot 64 at this portion of the upper rod, so that the above-mentioned converging side elements 66 and 68 holds the lower rod in place and protects it from disconnection from the upper rod.

Rear end of core rod 28 extends from the probe formed by two rods and has a shoulder 72. Shoulder 72 serves as a stopper or thrust element which rests on a rear end face 74 of upper rod 12.

Screwed onto threaded portion 62 of upper rod 12 is a cylindrical handle 76 which has inner thread 62a and bottom wall 76a. Cylindrical handle 76 has a central hole 80. The rear end 78 of core rod 28, which is located rearward from shoulder 72 passes through hole 80 and extends beyond the handle. This extending portion has a thread 82 and a nut 84 screwed onto this thread. Thus the cylindrical handle appears to be limited against axial displacements between shoulder 72 and nut 94 which form a sliding bearing of the handle. In other words, handle 76 can rotate with respect to core 28, but moved axially together with the latter.

Operation of the Bougie Shown in FIGS. 1 to 4

In use, the sterilized and assembled bougie, the parts of which assume positions shown in FIG. 1, is inserted into the urethra, i.e., handle 76 is screwed to the end onto threaded portion 62 of upper rod 12, the camming lobes are fit into their respective holes in the rods, and all three elements, i.e., both rods and the core element are positively locked together. Thus the bougie is inserted as an integral solid probe. Insertion of bougie 10 is facilitated by thin and flexible leader 52 which passes through the urethra first and thus guides the main part of the probe. The leader may have a length from 25 to 50 mm.

When insertion of the bougie is completed, cylindrical handle 76 is manually rotated in the unscrewing direction so that handle 76 moves rearward, i.e., to the right in FIG. 1. Since handle 76 is limited in the axial direction between shoulder 72 and nut 84, its axial displacement in the rearward direction will pull core 28 to the right, so that rear camming surfaces 42a and 42b of the core will slide to the right with respect to inclined camming surfaces 50a and 50b of through holes 44 and 46. This will cause expansion of the rods in the radial direction and thus dilate the urethra locally in the place where the stricture is located, or expand the entire urethra for subsequent insertion of other endourethral instruments.

For withdrawal of the bougie from the urethra, the urologist reverses rotation of handle 76. As a result, core 28 will move to the left in FIG. 1 until lobes 34 and 36 will tightly fit into respective holes 44 and 46. Although only two pairs of lobes and holes were described, those skilled in the art understand that the number of lobes and holes can be greater than the two shown in the drawings.

After the rods are closed and locked, the bougie can be easily extracted from the urethra.

If the bougie is made of metal, it is then disassembled and sterilized. A plastic disposable bougie is discarded.

Figure 6:
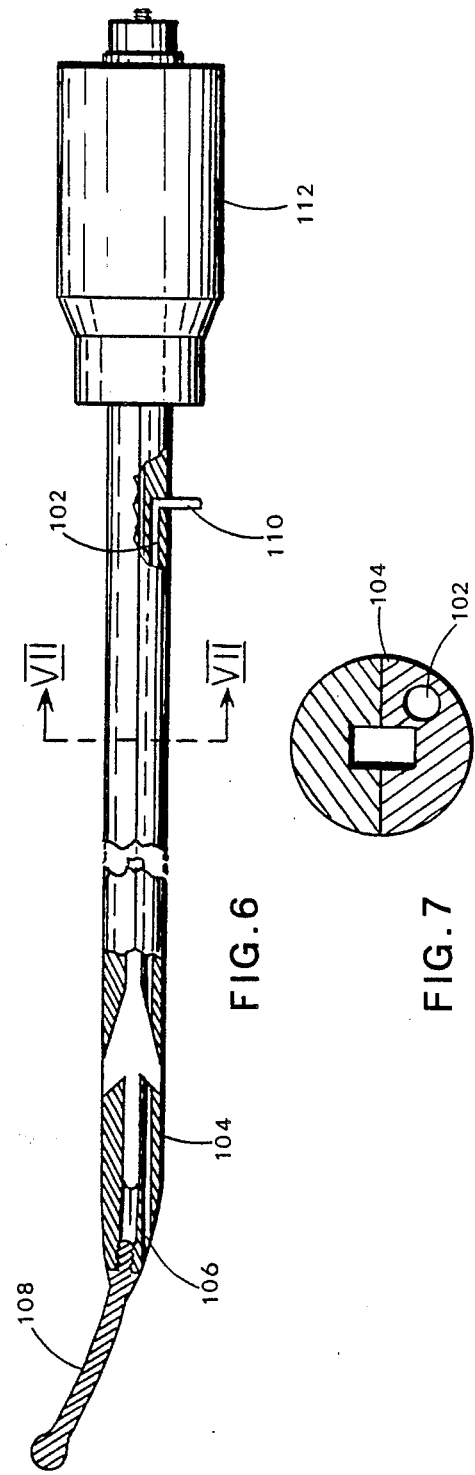
FIG. 6 is a partially-sectional side view of a bougie with an indicating channel formed in one of the rods.
Figure 7:
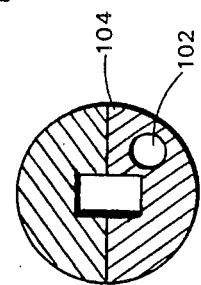
FIG. 7 is a cross-sectional view taken along line VII—VII of FIG. 6.

FIG. 5–7. Embodiment of the Bougie with Position Indicating Means

In some endourethral operations with the use of a bougie, it is important to know whether or not the bougie has penetrated into the patient's bladder. For this purpose an embodiment of the bougie shown in FIG. 5 is provided.

FIG. 5 shows bougie 90 which in general is the same as bougie 10 of FIGS. 1 to 4. It differs from it, however, in that guide slot 26 for core element 92 extends to the front end of the bougie, so that the front end 94 of core element 92 protrudes from the bougie and functions as a leader 52 of the bougie of FIG. 1. For this purpose, it has a smooth spherical head 96 which facilitates insertion and guiding of the bougie. Thus, core element 92 runs through the entire length of bougie 90 and has front end 94 as well as rear end 98 extending beyond the limits of the bougie's length. The length of extending front end 94 of the core element can be from 25 to 50 mm.

Core element 92 of bougie 90 has a through longitudinal opening 100 which passes through the entire length of core element 92. The remaining parts of bougie 90 are identical with those of the first embodiment and therefore do not require any description.

FIGS. 6 and 7 show an embodiment in which a through longitudinal opening 102 is formed not in core element 92, but rather in one of the rods, e.g., in a rod 104. Opening 102 starts at the tip of the probe, e.g. at a point 106 beneath the position of attachment of leader 108 to the tip of the bougie. Through opening 102 terminates at a point 110 on the side wall of rod 104 prior to the position of a handle 112.

The bougie of this embodiment operates in the same manner as the one describe in connection with FIG. 5.

Operation of the Bougie of FIG. 5

Bougie 90 shown in FIG. 5 operates exactly in the same manner as the one shown in FIGS. 1 to 4. The only difference is that when head 100 of guiding end 94 of core element 92 penetrates into the patient's bladder, the urine begins to flow through hole 100 and drips from rear end 98 of the bougie into a special tray 102 which can be placed under end 98 for this purpose. This dripping gives an indication to the urologist that the front end of the bougie has penetrated into the bladder.

In order to provide reliable passage of the urine through the core element, hole 100 should have a diameter not less than 1 mm. The core may have a height of 2.5 mm and a width of 2 mm. The diameter of the bougie in the locked position of the rods can be within the range of 5 to 8 mm.

Summary, Ramifications, Scope

Although the invention has been shown and described in the form of specific embodiments, it is understood that these embodiments, their parts, materials and configurations were given only as examples, and many other modifications of the bougie of the invention are possible. For example, an increased-diameter portion can be formed on the lower rod instead of the upper rod. Camming lobes 34 and 36 may have different geometry. Lobes 34 and 36 may have asymmetric positions with respect to each other. Handle 76 can be fixed axially with respect to core element 28 in a different manner, and a different locking means, such as a lock washer can be used instead of nut 84. The flexible leader can be threaded onto the tip of the probe, and the probes themselves can be pivotally interconnected through a disengageable hook-and-loop pivotal joint. Therefore, the scope of the invention should be determined, not by the examples, given, but by the appended claims and their legal equivalents.

We claim:

1. An instrument comprising
   (a) a probe having a first end, a second end, and a central portion therebetween,
   the probe comprising a plurality of rods, the rods being bound together at the first end of the probe, the rods being separable at the central portion of the probe, each of said rods comprising a camming surface disposed thereon,
   (b) means for restricting radial movement of the rods at the second end of the probe,
   (c) means for separating the rods at the central portion, said means for separating comprising
   movable cams, said cams being disposed adjacent and between the rods, the cams having camming surfaces,
   an actuator for moving the cams axially with respect to the rods, and
   means for connecting the actuator to the cams, the cams being movable by the actuator to bring the camming surfaces of the cams together with the camming surfaces of the rods, thereby separating the rods at the central portion of the probe, and
   (d) means for locking the rods in an unseparated position.

2. The instrument of claim 1 wherein the number of cams equals the number of rods, each of said cams having one camming surface.

3. The instrument of claim 1 wherein each rod comprises a plurality of camming surfaces.

4. The instrument of claim 1 wherein the means for locking comprises a locking surface on each of the rods and corresponding locking surfaces on the cams, the cam locking surfaces contacting the rod locking surfaces when the rods are in the unseparated position.

5. An instrument comprising:
   (a) a probe having a first end, a second end, and a central portion therebetween,
   the probe comprising a plurality of rods, the rods being bound together at the first end of the probe, the rods being separable at the central portion of the probe, each of said rods comprising a camming surface disposed thereon, (b) means for restricting radial movement of the rods at the second end of the probe, (c) means for separating the rods at the central portion, said means for separating comprising movable cams, said cams being disposed adjacent and between the rods, the cams having camming surfaces, an actuator for moving the cams axially with respect to the rods, and means for connecting the actuator to the cams, the cams being movable by the actuator to bring the camming surfaces of the cams together with the camming surfaces of the rods, thereby separating the rods at the central portion of the probe, said means for connecting the actuator to the cams being a core element disposed between the rods, the cam locking surfaces facing said core element and forming an acute angle with the core element, and (d) means for locking the rods in an unseparated position, the means for locking comprising a locking surface on each of the rods and corresponding locking surfaces on the cams, the cam locking surfaces contacting the rod locking surfaces when the rods are in the unseparated position.

6. The instrument of claim 5 wherein the core element extends beyond the rods at the first end of the probe to form a leader.

7. The instrument of claim 5 wherein the rods have grooves formed therein and the core element is disposed in the grooves.

8. The instrument of claim 7 wherein the probe has a substantially circular cross-section.

9. The instrument of claim 7 wherein the number of rods is two, the actuator comprising an enlarged portion of one of said rods at the second end of the probe, the enlarged portion having external threads and a radial slot, one end of the other rod being disposed in the radial slot, said means for restricting radial movement comprising the radial slot.

10. The instrument of claim 9 wherein the actuator further comprises a threaded handle surrounding the enlarged portion and mating with the threads on the enlarged portion, the means for connecting the actuator to the cams being a core element disposed between the rods, the core element being attached to the handle so that the handle can rotate with respect to the core element but cannot move axially with respect to the core element, whereby rotation of the handle on the enlarged portion moves the cored element axially with respect to the rods.

11. The instrument of claim 10 wherein the radial slot has converging walls, the end of the other rod being held in the radial slot by the converging walls.

12. The instrument of claim 11 further comprising means for indicating that the probe has penetrated a patient's bladder.

13. The instrument of claim 1 further comprising a leader disposed at the first end of the probe.

14. The instrument of claim 13 wherein the leader is formed integrally with the rods.

15. The instrument of claim 13 further comprising means for attaching and detaching the leader to and from the probe.

16. An instrument comprising:

(a) a probe having a first end, a second end, and a central portion therebetween;

the probe comprising two rods, the rods being bound together at the first end of the probe, the rods being separable at the central portion of the probe, each of said rods comprising a camming surface disposed thereon, (b) means for restricting radial movement of the rods at the second end of the probe, (c) means for separating the rods at the central portion, said means for separating comprising:

movable cams, said cams being disposed adjacent and between the rods, the cams having camming surfaces, an actuator for moving the cams axially with respect to the rods, the actuator comprising an enlarged portion of one of said rods at the second end of the probe, the enlarged portion having external threads in a radial slot, an end of the other rod being disposed in the radial slot, said means for restricting radial movement comprising the radial slot, and (d) means for locking the rods in an unseparated position.

17. The instrument of claim 16 wherein the means for locking comprises a locking surface on each of the rods and corresponding locking surfaces on the cams, the cam locking surfaces contacting the rod locking surfaces when the rods are in the unseparated position.

18. The instrument of claim 17 wherein said means for connecting the actuator to the cams is a core element disposed between the rods, the cam locking surfaces facing said core element and forming an acute angle with the core element.

19. The instrument of claim 16 wherein the actuator further comprises a threaded handle surrounding the enlarged portion and mating with the threads on the enlarged portion, the means for connecting the actuator to the cams being a core element disposed between the rods, the core element being attached to the handle so that the handle can rotate with respect to the core element but cannot move axially with respect to the core element, whereby rotation of the handle on the enlarged portion moves the core element axially with respect to the rods.

20. The instrument of claim 19 wherein the probe has a substantially circular cross-section.

21. The instrument of claim 11 wherein the radial slot has converging walls, the end of the other rod being held in the radial slot by the converging walls.

22. An instrument comprising:

(a) a probe having a first end, a second end, and a central portion therebetween, the probe comprising a plurality of rods, the rods being bound together at the first end of the probe, the rods being separable at the central portion of the probe, each of said rods comprising a camming surface disposed thereon, (b) means for restricting radial movement of the rods at the second end of the probe, (c) means for separating the rods at the central portion, said means for separating comprising movable cams, said cams being disposed adjacent and between the rods, the rods having camming surfaces, an actuator for moving the cams axially with respect to the rods, and means for connecting the actuator to the cams, the cams being movable by the actuator to bring the camming surfaces of the cams together with the camming surfaces of the rods, thereby separating the rods at the central portion of the probe, (d) means for locking the rods in an unseparated position, and (e) means for indicating that the probe has penetrated a patient's bladder.

23. The instrument of claim 22 wherein the means for connecting the actuator to the cams is a core element between the rods, the means for indicating comprising a longitudinal channel formed in the core element having an inlet at the first end of the probe and an outlet at the second end of the probe.

24. The instrument of claim 22 wherein the means for indicating comprises a longitudinal channel formed in one of the rods, the channel having an inlet at the first end of the probe and an outlet at the second end of the probe.

25. An instrument comprising (a) a probe having a first end, a second end, and a central portion therebetween, the probe comprising a plurality of rods, the rods being bound together at the first end of the probe, the rods being separable at the central portion of the probe, each of said rods comprising a camming surface disposed thereon, (b) means for restricting radial movement of the rods at the second end of the probe, and (c) means for separating the rods at the central portion, said means for separating comprising (i) movable cams disposed adjacent and between the rods, said cams having camming surfaces, (ii) an actuator for moving the cams axially with respect to the rods, (iii) means for locking the rods in an unseparated position, and (iv) means for connecting the actuator to the cams, said means for connecting comprising a core element between the rods, the cams movable by the actuator to bring the camming surfaces of the cam together with the camming surfaces of the rods, thereby separating the rods at the central portion of the probe.

26. The instrument of claim 25 wherein the number of cams equals the number of rods, each of said cams having one camming surface.

27. The instrument of claim 25 wherein each rod comprises a plurality of camming surfaces.

28. The instrument of claim 25 wherein the means for locking comprises a locking surface on each of the rods and corresponding locking surfaces on the cams, the cam locking surfaces contacting the rod locking surfaces when the rods are in the unseparated position.

29. The instrument of claim 28 wherein the cam locking surfaces face the core element and form an acute angle with the core element 30. The instrument of claim 25 further comprising a leader disposed at the first end of the probe.

31. The instrument of claim 30 wherein the leader is formed integrally with the rods.

32. The instrument of claim 30 further comprising means for attaching and detaching the leader to and from the probe.

33. An instrument comprising:

(a) a probe having a first end, a second end, and a central portion therebetween;

the probe comprising two rods, the rods being bound together at the first end of the probe, the rods being separable at the central portion of the probe, each of said rods comprising a camming surface disposed thereon, (b) means for restricting radial movement of the rods at the second end of the probe, and (c) means for separating the rods at the central portion, said means for separating comprising:

(i) movable cams being disposed adjacent and between the rods, said cams having camming surfaces, (ii) an actuator for moving the cams axially with respect to the rods, the actuator comprising an enlarged portion of one of said rods at the second end of the probe, the enlarged portion having external threads in a radial slot, an end of the other rod being disposed in the radial slot, said means for restricting radial movement comprising the radial slot, (iii) means for locking the rods in an unseparated position, and (iv) means for connecting the actuator to the cams, said means for connecting comprising a core element between the rods, and the cams being movable by the actuator to bring the camming surfaces of the cams together with the camming surfaces of the rods, thereby separating the rods at the central portion of the probe.

34. The instrument of claim 33 wherein the actuator further comprises a threaded handle surrounding the enlarged portion and mating with the threads on the enlarged portion, the means for connecting the actuator to the cams being a core element between the rods, the core element being attached to the handle so that the handle can rotate with respect to the core element but cannot move axially with respect to the core element whereby rotation of the handle on the enlarged portion moves the core element axially with respect to the rods.

35. The instrument of claim 33 wherein the radial slot has converging walls, the end of the other rod being held in the radial slot by the converging walls.

36. An instrument comprising:

(a) a probe having a first end, a second end, and a central portion therebetween;

the probe comprising a plurality of rods, the rods being bound together at the first end of the probe, the rods being separable at the central portion of the probe, each of said rods comprising a camming surface disposed thereon, (b) means for restricting radial movement of the rods at the second end of the probe, (c) means for separating the rods at the central portion, said means for separating comprising:

(i) movable cams disposed adjacent and between the rods, said cams having camming surfaces, (ii) an actuator for moving the cams axially with respect to the rods, (iii) means for locking the rods in an unseparated position, and (iv) means for connecting the actuator to the cams, said means for connecting comprising a core element between the rods, the cams being movable by the actuator to bring the camming surfaces of the cams together with the camming surfaces of the rods, thereby separating the rods at the central portion of the probe, and (d) means for indicating that the probe has penetrated a patient's bladder.

37. The instrument of claim 36 wherein the means for connecting the actuator to the cams is a core element disposed between the rods, the means for indicating comprising a longitudinal channel formed in the core element having an inlet at the first end of the probe and an outlet at the second end of the probe.

38. The instrument of claim 36 wherein the means for indicating comprises a longitudinal channel formed in one of the rods, the channel having an inlet at the first end of the probe and an outlet at the second end of the probe.

* * * * *